(12) United States Patent
Sears et al.

(10) Patent No.: US 7,641,472 B2
(45) Date of Patent: Jan. 5, 2010

(54) FORCE-RESPONSIVE ORTHODONTIC BRACKETS AND SYSTEMS AND METHODS

(75) Inventors: Robert Steven Sears, Round Hill, VA (US); William Stuart Trimmer, Hillsborough, NJ (US)

(73) Assignee: Right Force Orthodontics Inc., Hillsborough, NJ (US)

( * ) Notice: Subject to any disclaimer, the term of this patent is extended or adjusted under 35 U.S.C. 154(b) by 546 days.

(21) Appl. No.: 11/596,593

(22) PCT Filed: May 10, 2005

(86) PCT No.: PCT/US2005/015969

§ 371 (c)(1),
(2), (4) Date: Nov. 15, 2006

(87) PCT Pub. No.: WO2005/115265

PCT Pub. Date: Dec. 8, 2005

(65) Prior Publication Data

US 2007/0231767 A1    Oct. 4, 2007

Related U.S. Application Data

(60) Provisional application No. 60/571,690, filed on May 17, 2004.

(51) Int. Cl.
*A61C 3/00* (2006.01)
(52) U.S. Cl. .............................................. 433/8; 433/9
(58) Field of Classification Search ............... 433/8–17, 433/24
See application file for complete search history.

(56) References Cited

U.S. PATENT DOCUMENTS

| 3,052,027 | A | 9/1962 | Wallshein |
| 3,250,003 | A | 5/1966 | Collito |
| 4,186,488 | A | 2/1980 | Wallshein |
| 4,674,978 | A | 6/1987 | Acevedo |
| 5,562,448 | A | 10/1996 | Mushabae |
| 6,402,707 | B1 | 6/2002 | Ernst |

FOREIGN PATENT DOCUMENTS

WO    WO 03/096922    11/2003

OTHER PUBLICATIONS

International Search Report mailed Sep. 18, 2007.
International Search Report mailed Sep. 29, 2005 in PCT/US05/015969.
Written Opinion mailed Sep. 29, 2005 in PCT/US05/015969.

*Primary Examiner*—John J Wilson
(74) *Attorney, Agent, or Firm*—Nixon & Vanderhye P.C.

(57) ABSTRACT

Force magnitudes and/or directions may be determined objectively using orthodontic brackets having an elastomeric member which allows one portion of the bracket to be resiliently moveable relative to at least on other portion of the bracket. In a preferred embodiment, the brackets include a lower base member, an upper bracket member, and an elastomeric layer interposed between the lower base and upper bracket members. The orthodontic bracket is advantageously employed as part of a system whereby the orthodontic bracket includes a force indicator which distorts in response to relative movement between the at least one and other portions of the bracket to provide an indication of force applied to the bracket. An optical detector may be provided to optically detect the indicator and issue an output signal indicative of the relative resilient movement between the lower base and upper bracket members. A processor receives the output signal from the optical detector to provide an indication of magnitude and/or direction of the force applied to the upper bracket member.

28 Claims, 5 Drawing Sheets

FORCE-RESPONSIVE ORTHODONTIC BRACKETS AND SYSTEMS AND METHODS

This application is the US national phase of international application PCT/US2005/015969 filed 10 May 2005 which designated the U.S. and claims benefit of U.S. 60/571,690, dated 17 May 2004, the entire content of which is hereby incorporated by reference.

CROSS-REFERENCE TO RELATED APPLICATION

This application is based on, and claims priority benefits from, U.S. Provisional Application Ser. No. 60/571,690 filed on May 17, 2004, the entire content of which is expressly incorporated hereinto by reference.

FIELD OF THE INVENTION

The present invention relates generally to the field of orthodontics. In especially preferred embodiments, the present invention relates to orthodontic brackets which include a force-responsive component by which the magnitude and/or direction of an applied force may be determined optically.

BACKGROUND AND SUMMARY OF THE INVENTION

Orthodontic brackets typically are attached to individual teeth and connected to an archwire so as to apply appropriate force over time to move and straighten teeth. Specifically, teeth are moved and rotated by applying forces to the brackets via the archwire. Periodic visits to the orthodontist are therefore required so that the assembly may be checked and adjusted to ensure the proper amount and direction of force is being applied by the archwire to the teeth via the brackets. Adjustment of the archwire is, however, a highly subjective endeavor. Orthodontists therefore gain practical knowledge of the amount and direction of force that is needed for an individual orthodontic patient.

It would, however, be highly advantageous if the magnitude and direction of force applied to an orthodontic bracket could be determined objectively. It is towards fulfilling such a need that the present invention is directed.

Broadly, the present invention is embodied in a force-responsive orthodontic bracket. More specifically, the orthodontic bracket of the present invention allows for the objective determination of the magnitude and/or direction of force applied to the tooth to which the bracket is attached. The present invention is therefore preferably embodied in orthodontic brackets having an elastomeric member which allows one portion of the bracket to be resiliently moveable relative to at least one other portion of the bracket. The bracket preferably includes an indicator (e.g., fiducial marks) which distort in response to movement of the bracket portions relative to one another, whereby the indicator distortion is indicative of the magnitude and/or direction of a force applied to the bracket.

In especially preferred embodiments, the present invention includes a force-responsive orthodontic bracket having a lower base member, an upper bracket member, and an elastomeric layer interposed between the lower base and upper bracket members. The elastomeric layer therefore comprises an elastomeric member which allows the upper bracket member to be moveable resiliently relative to the lower base member.

The orthodontic brackets of the present invention are advantageously employed as part of a system whereby the bracket includes an indicator for an indicator of force applied to the upper bracket member sufficient to cause resilient movement of the upper bracket member relative to the lower base member. An optical detector may be provided to optically detect the indicator and issue an output signal indicative of the relative resilient movement between the lower base and upper bracket members. A processor receives the output signal from the optical detector to provide an indication of magnitude and/or direction of the force applied to the upper bracket member.

These and other aspects and advantages will become more apparent after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein.

DETAILED DESCRIPTION OF THE INVENTION

Figure 1:
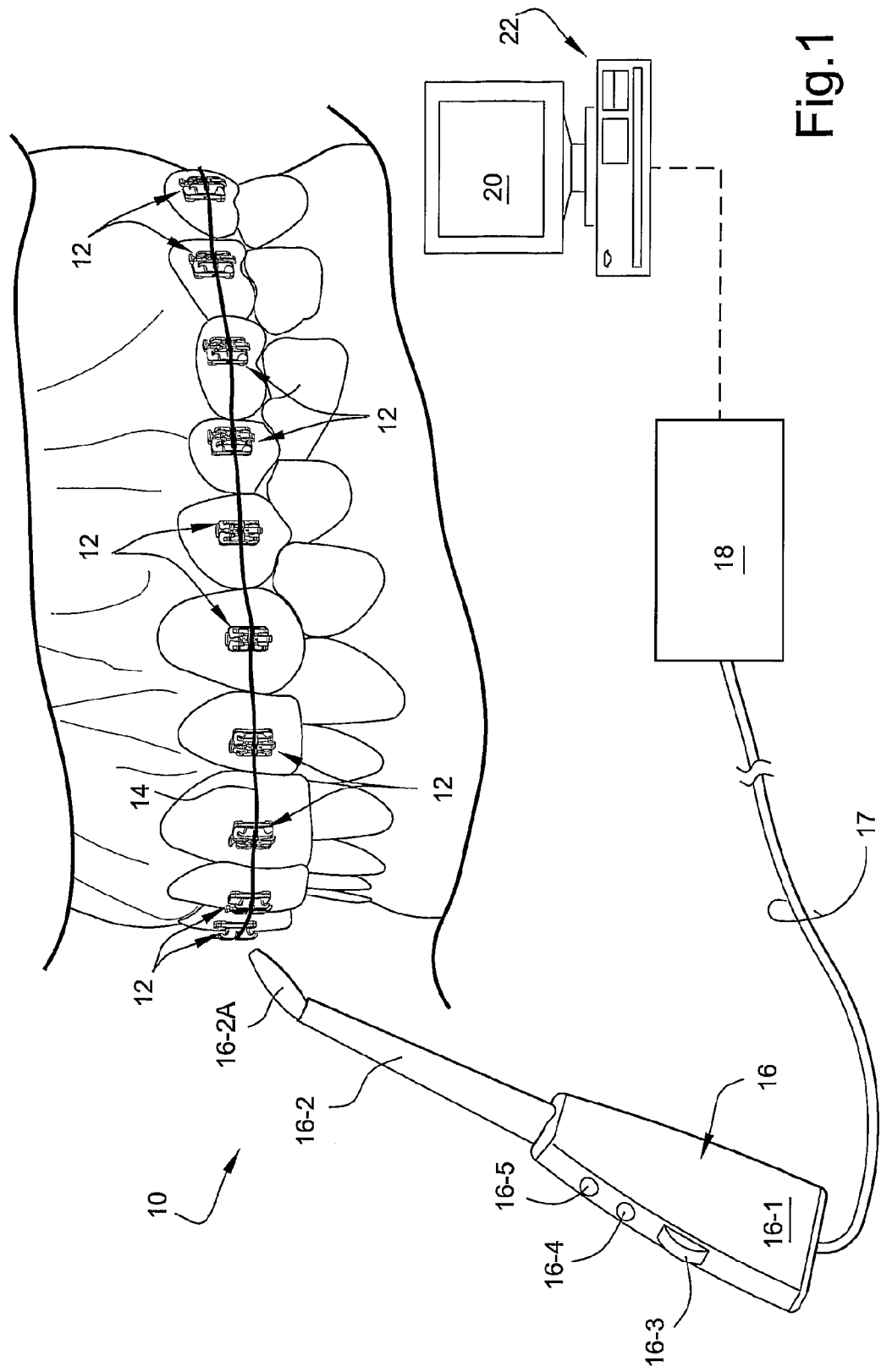
FIG. 1 is a schematic perspective view of a system which employs the force-responsive brackets of the present invention.

Accompanying FIG. 1 depicts schematically a system 10 according to the present invention which is especially adapted to detect and present the magnitude and/or direction of force associate with individual ones of the orthodontic brackets 12 which are bonded to the front surfaces of respective teeth in a patient's mouth. As will be explained in greater detail below, the individual brackets 12 are provided with fiducial markings that are indicative of the magnitude and/or direction of force applied to the brackets 12 by means of the archwire 14.

Generally, according to the present invention, the fiducial markings may be detected optically by means of a hand-held optical detector 16 which is connected operatively to a central processor 18 by signal line 17. The central processor 18 thus receives an output signal generated by means of the optical detector 16 via the signal line 17 and is programmed with the necessary algorithms which translate the output signal representative of the optically detected indication provided by the fiducial marks into a force magnitude and/or vector that may be displayed to the attending orthodontist, for example, via a conventional monitor 20 associated with personal computer 22. Alternatively, the output signal generated by means of the optical detector 16 may be transmitted to the processor 18 wirelessly, for example, using a RF (radio frequency) link.

The hand-held optical detector 16 most preferably includes a proximal handle portion 16-1 and a distal light-emitting wand 16-2. A trigger switch 16-3 is provided on the proximal handle portion 16-1 to allow the orthodontist to activate the wand 16-2 in order to take an optical reading of a particular one of the brackets 12 via the wand tip 16-2a. Light-emitting diodes (LED's) 16-4, 16-5 may also be provided in the handle portion 16-1 and most preferably emit different colors (e.g., red and green) to provide a visual indication to the orthodontist that a satisfactory optical reading of a particular bracket 12 has ensued. The LED's 16-4, 16-5 may also be used to indicate if an acceptable force has been applied to a particular bracket 12. To accomplish such indication, the processor 18 would compare the forces and/or torques applied to the bracket and sensed by the detector 16 to forces and/or torques stored in memory and associated with that particular treatment plan for the individual patient.

Figure 2:
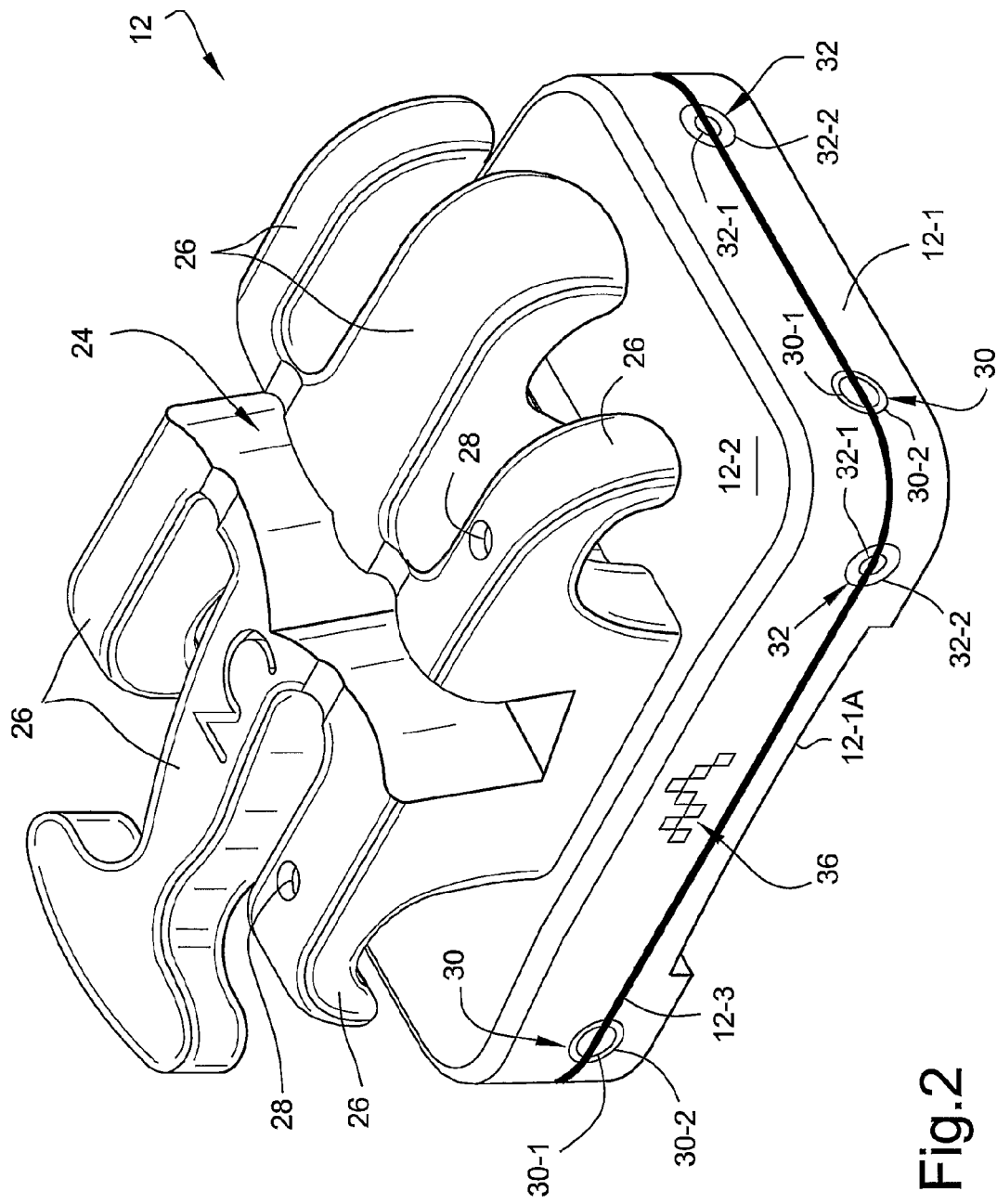
FIG. 2 is a perspective view of an exemplary force-responsive orthodontic bracket according to the present invention.
Figure 3:
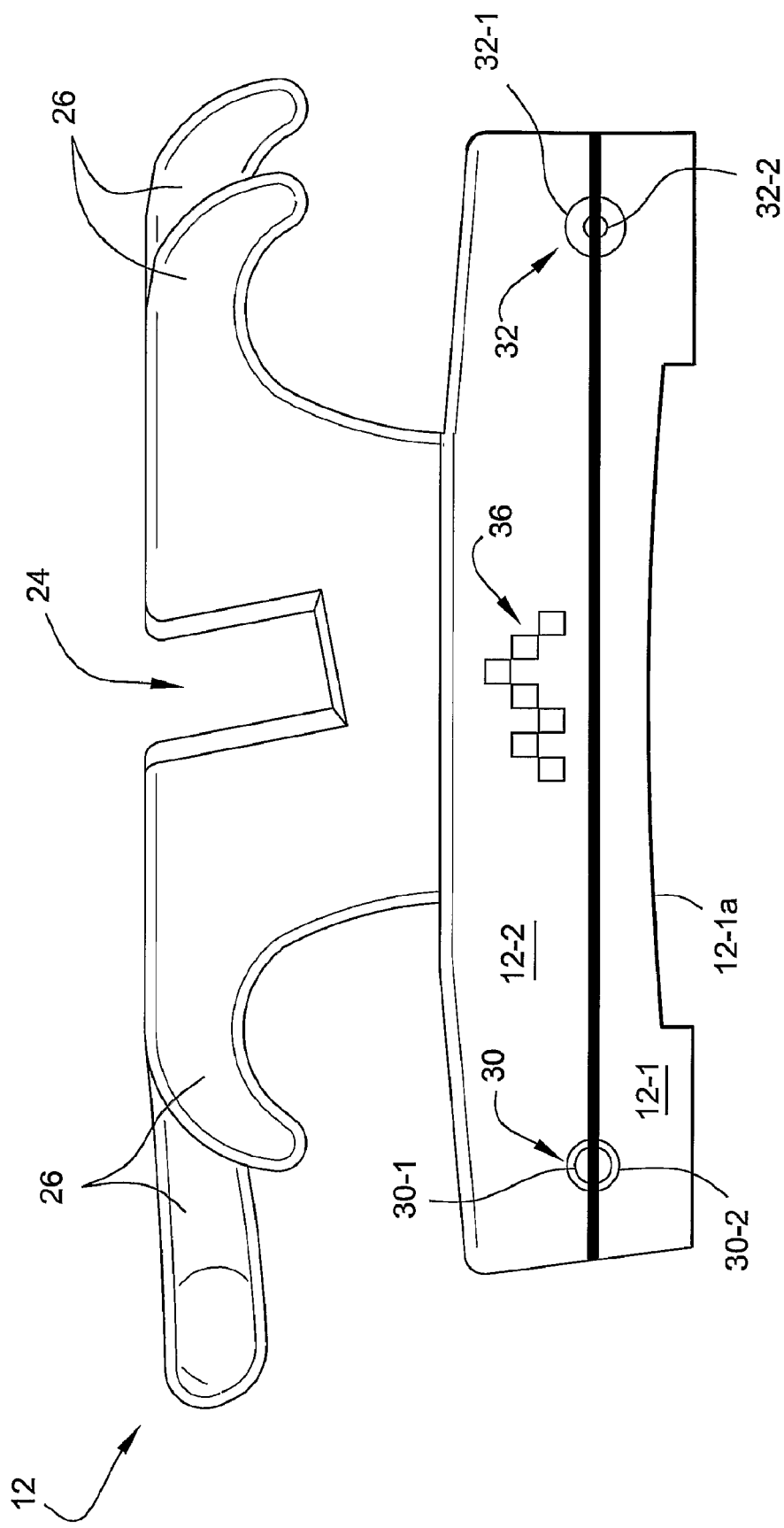
FIG. 3 is a side elevation view of the orthodontic bracket depicted in FIG. 2.

One preferred embodiment of the bracket 12 according to the present invention is depicted in accompanying FIGS. 2 and 3. In this regard, it will be observed that the bracket 12 comprises a lower base member 12-1, an upper bracket member 12-2, and an intermediate elastomeric layer 12-3 which resiliently joins the upper bracket member 12-2 to the lower base member 12-1 to thereby allow for slight, but meaningful, relative resilient movement therebetween. Virtually any elastomeric material compatible with orthodontic applications may be used for layer 12-3 and may include for example, EPDM rubber, silicone rubber, and polyester elastomers to name just a few. Suffice it to say that the particular elastomeric material that is employed may be selected by those of ordinary skill in this art without undue experimentation based on the physical properties of the same.

As is conventional, the upper bracket member 12-2 includes a slot 24 for receiving the archwire 14 as well as a plurality of posts 26 and apertures 28 which may be used by the orthodontist to secure additional wires in order to impart the proper force for transfer to the tooth to which the bracket 12 is bonded. The lower bracket member 12-1 most preferably includes a recessed surface 12-1a formed therein to accommodate a bonding material to secure rigidly the base member 12-1 to, an underlying tooth so as to, in turn, securely anchor the bracket 12 to the tooth.

The lower base member 12-1 and upper bracket member 12-2 include fiducial marks 30, 32 on multiple visible surface thereof which are divided by the elastomeric layer 12-3 to form upper and lower mark segments 30-1, 32-1 and 30-2, 32-2, respectively. In the absence of applied force, therefore, the upper and lower segments 30-1, 30-2 and 32-1, 32-2 of the fiducial marks 30, 32, respectively, will be aligned with one another. That is, no misregistration between the upper and lower segments 30-1, 30-2 and 32-1, 32-2 of the fiducial marks 30, 32, respectively, will be visibly present.

In response to the application of force, for example via the archwire 14, to the upper bracket member 12-2, the upper and lower segments 30-1, 30-2 and 32-1, 32-2 of the fiducial marks 30, 32, respectively, will therefore become distorted (i.e., misregistered) in dependence upon the magnitude and direction of the applied force by virtue of the elastomeric layer 12-3 which allows the upper bracket member 12-2 to move resiliently with respect to the lower base member 12-1. It is this relative misregistration between the upper and lower segments 30-1, 30-2 and 32-1, 32-2 of the fiducial marks 30, 32, respectively, that may be detected optically by means of the optical detector 16. The relative misregistration between the upper and lower segments 30-1, 30-2 and 32-1, 32-2 of the fiducial marks 30, 32, respectively, detected by the optical detector 16 may thus be communicated to the processing unit 18 wherein the magnitude and/or direction of applied force to a particular bracket is calculated. An appropriate signal is then sent to the personal computer 22 so that the magnitude and/or direction of applied force may be displayed for the orthodontist.

The fiducial marks 30, 32 are shown as being in the form of multiple differently sized concentric circles. Such an arrangement therefore allows comparison of one of the upper and lower segments 30-1, 30-2 and 32-1, 32-2 of the fiducial marks 30, 32, respectively, to another so as to arrive at relative misregistrations therebetween. In such a manner, therefore, the magnitude of the applied force may be detected as well as the direction of the applied force relative to six degrees of freedom, namely three mutually orthogonal axes in addition to torque about such axes.

The brackets 12 of the present invention may also carry unique identification indicia 36 which will permit an orthodontist to electronically "tag" each bracket and associate the various force magnitudes and directions thereto. Such unique identification of the individual brackets 12 by the indicia 36 will also allow a historical analysis of its individual movement throughout the orthodontic treatment procedure to be tracked.

The fiducial marks 30, 32 may be of any type suitable for optical detection by means of the detector 16. Thus, for example, the fiducial marks 30, 32 may be formed of any visible media which capable of detection by the optical detector 16, for example, by means of video capture using a miniature video camera within the tip 16-2a of the detector wand 16-2. Alternatively or additionally, the fiducial marks may be formed of phosphorescent or fluorescent media so as to be more visible when irradiated by ultraviolet (UV) light emitted by the optical detector wand 16-2. In such a case, therefore, the detector 16 may be operable (e.g., by operating the trigger switch 16-3 thereof) so as to illuminate the desired bracket 12 with UV radiation thereby causing the fiducial marks 30, 32 to phosphoresce or fluoresce as the case may be, following which the UV radiation from the wand tip 16-2a may be turned off. An optical comparison may then be made between the fiducial marks 30, 32 based their "on" image and their "off" image. Again, alternatively or additionally, the wand tip 16-2a of the optical detector wand 16-2 may emit laser radiation which scans the fiducial marks 30, 32 so as to detect misregistry therebetween.

Figure 4:
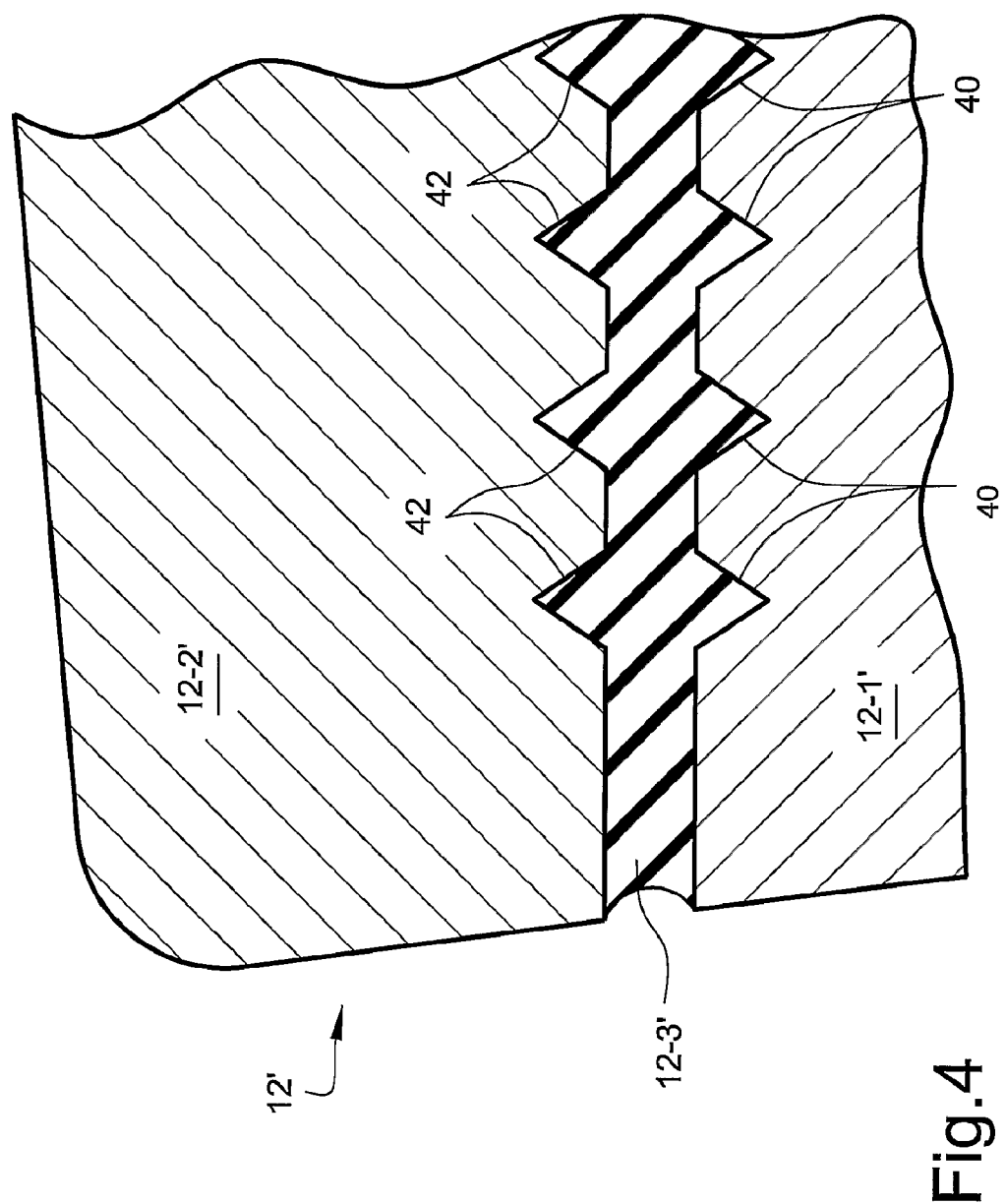
FIG. 4 is a greatly enlarged partial side cross-sectional view of an alternative embodiment of an orthodontic bracket according to the present invention.

An alternative embodiment of a bracket 12' in accordance with the present invention is shown in accompanying FIG. 4. As depicted, the bracket 12' is similar to the bracket 12 as discussed previously in that it includes a lower base member 12-1', an upper bracket member 12-2', and an intermediate elastomeric layer 12-3' which resiliently joins the upper bracket member 12-2' to the lower base member 12-1' to thereby allow for slight, but meaningful, relative resilient movement therebetween. However, instead of or in addition to the fiducial marks 30, 32, there are provided a series of opposed grooves 40, 42 formed respectively in the lower base member 12-1' and the upper bracket member 12-2'. These grooves 40-42 are registered in the absence of any force applied to the upper bracket member 12-2', but will become slightly misregistered with one another in response to the application of force to the upper bracket member 12-2'. That is, the upper bracket member 12-2' is able to be resiliently displaced relative to the lower base member 12-1' by virtue of the intermediate elastomeric layer 12-3' which joins the members 12-1' and 12-2' one to another. Such misregistration of the grooves 40, 42 may thus be detected optically by the optical detector 16 in a manner similar to that described previously. The grooves 40, 42 also assist structurally to enhance anchoring of the elastomeric layer 12-3' to each of the lower base and upper bracket members 12-1' and 12-2', respectively. As shown, the grooves 40, 42 are opposed V-shaped elements, but other geometric forms such as rectangularly or hemispherically shaped elements, could be employed for the purpose of the present invention.

Figure 6:
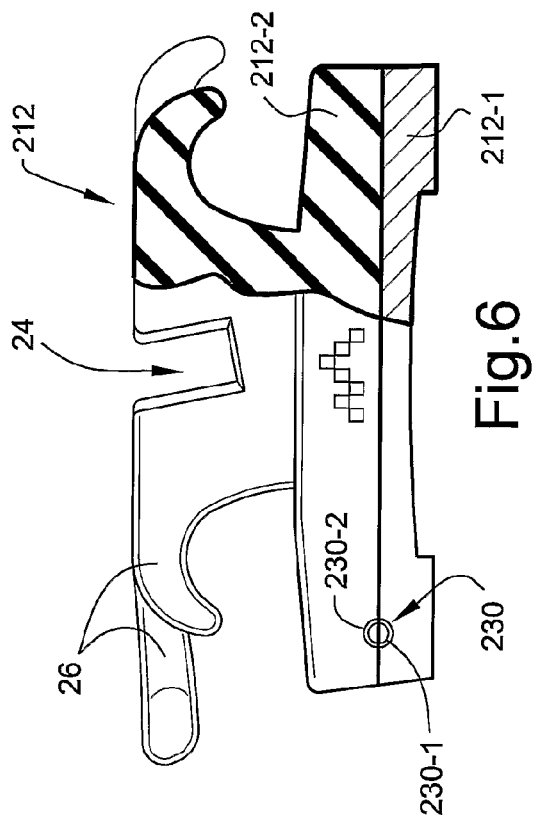
FIG. 6 is an enlarged partial side cross-sectional view of another alternative embodiment of an orthodontic bracket according to the present invention.
Figure 5:
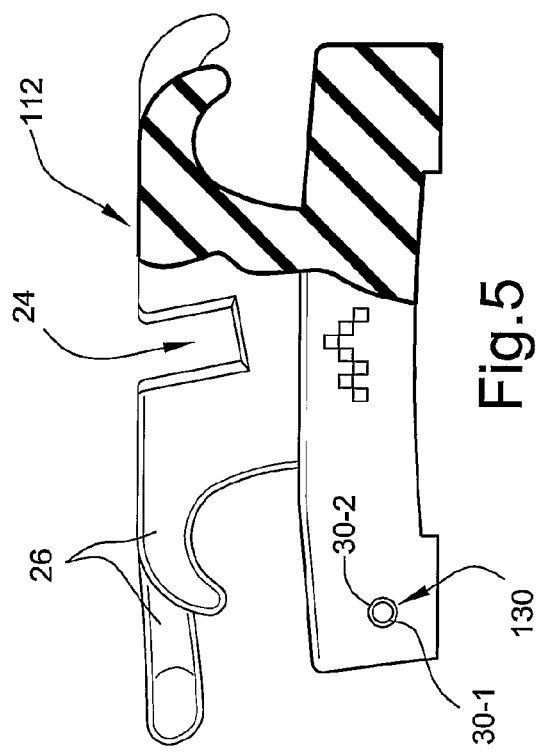
FIG. 5 is an enlarged partial side cross-sectional view of another alternative embodiment of an orthodontic bracket according to the present invention.
Figure 7:
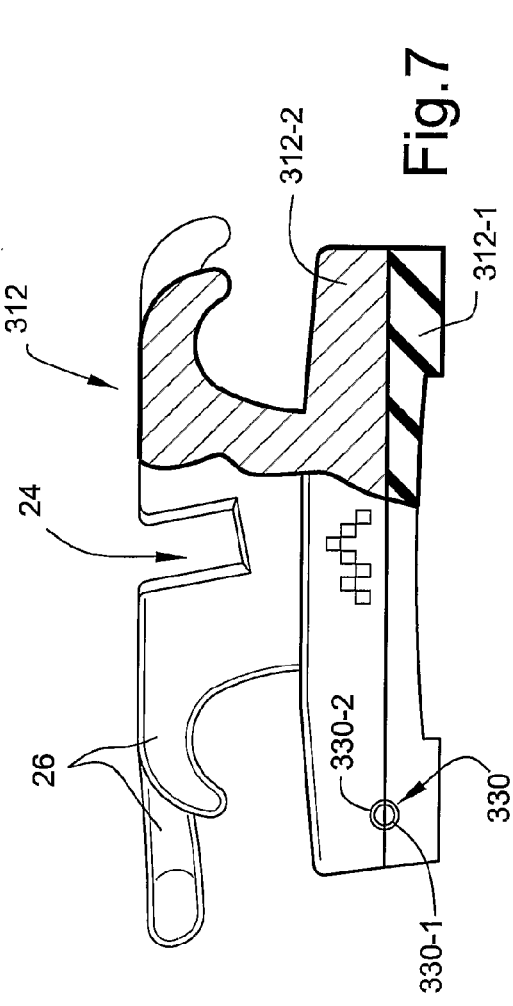
FIG. 7 is an enlarged partial side cross-sectional view of yet another alternative embodiment of an orthodontic bracket according to the present invention.

Accompanying FIGS. 5-7 depict alternative embodiments in accordance with the present invention. In this regard, it will be observed from FIG. 5 that the entire bracket 112 is formed of an elastomeric material and includes a plurality of fiducial marks 130 comprised of concentrically disposed inner and outer marks 130-1, 130-2, respectively. In this regard, only a single fiducial mark 130 is visible in FIG. 5, it being understood that several such fiducial marks 130 will be provided in the manner as described previously. The fiducial marks 130 are either imprinted on a visible surface of the bracket 112 or embedded physically therewithin. In this latter possibility, the elastomeric material from which the bracket 112 is formed is most preferably translucent or transparent so that the detector 16 may visibly detect the fiducial mark 130 embedded therewithin. Forces applied to the bracket 112 will therefore cause portions of the bracket to be moveable or flexed thereby distorting the fiducial marks 130. The amount and direction of such distortion may then be detected by the detector 16 so as to detect the magnitude and/or direction of the applied force.

FIGS. 6 and 7 depict further alternative embodiments of brackets 212 and 312, respectively in accordance with the present invention. In this regard, the bracket 212 of FIG. 6 is comprised of a lower base member 212-1 which is formed of metal and an upper bracket member 212-2 formed entirely of an elastomeric material. The bracket 212 includes a plurality of fiducial marks 230 comprised of concentrically disposed inner and outer marks 230-1, 230-2, respectively. In this regard, only a single fiducial mark 230 is visible in FIG. 6, it being understood that several such fiducial marks 230 will be provided in the manner as described previously.

Accompanying FIG. 7 on the other hand depicts a bracket 312 in accordance with the present invention where the lower base member 312-1 is formed of an elastomeric material and the upper bracket member 312-2 is formed of metal. The bracket 312 includes a plurality of fiducial marks 330 comprised of concentrically disposed inner and outer marks 330-1, 330-2, respectively. In this regard, only a single fiducial mark 230 is visible in FIG. 7, it being understood that several such fiducial marks 330 will be provided in the manner as described previously.

In both of the embodiments depicted in FIGS. 6 and 7, therefore, the upper bracket members 212-2 and 312-2 are capable of resilient movement relative to the lower base members 212-1 and 212-2, respectively.

Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. An orthodontic bracket comprising:
   a lower base member,
   an upper bracket member,
   an elastomeric layer interposed between said lower base and upper bracket members, and
   at least one fiducial mark as an indicator for indicating relative movement between the lower base and upper bracket members, wherein
   the at least one fiducial mark comprises registered lower and upper mark segments on the lower base and upper bracket members, respectively, wherein misregistry between the lower and upper mark segments is indicative of a force applied to the upper bracket member.

2. The orthodontic bracket as in claim 1, wherein the at least one fiducial mark is formed of a phosphorescent or fluorescent material.

3. The orthodontic bracket as in claim 1, wherein the at least one fiducial mark comprises registered grooves formed on opposing surfaces of the lower base and upper bracket members.

4. The orthodontic bracket as in claim 3, wherein the registered grooves are V-shaped, rectangularly shaped or hemspherically shaped.

5. The orthodontic bracket as in claim 1, wherein the upper bracket member comprises at least one slot for receiving an archwire.

6. The orthodontic bracket as in claim 1, wherein the lower base member includes a recess.

7. An orthodontic bracket comprising:
   a lower base member,
   an upper bracket member,
   elastomer means interposed between the lower base and upper bracket members for allowing resilient movement of the upper bracket member relative to the lower base member in response to a force applied to the upper bracket member, and
   means indicative of said resilient relative movement between the upper bracket and lower base members, wherein
   the movement-indicative means comprises at least one fiducial mark for indicating relative movement between the lower base and upper bracket members, and wherein
   the at least one fiducial mark comprises registered lower and upper mark segments on the lower base and upper bracket members, respectively, wherein misregistry between the lower and upper mark segments is indicative of magnitude and/or direction of a force applied to the upper bracket member.

8. The orthodontic bracket as in claim 7, wherein the at least one fiducial mark is formed of a phosphorescent or fluorescent material.

9. The orthodontic bracket as in claim 7, wherein the at least one fiducial mark comprises registered grooves formed on opposing surfaces of the lower base and upper bracket members.

10. The orthodontic bracket as in claim 9, wherein the registered grooves are V-shaped, rectangularly shaped or hemspherically shaped.

11. An orthodontic system comprising:
    at least one orthodontic bracket which is comprised of an elastomeric member which allows at least one portion of the bracket to be resiliently movable relative to at least one other portion of the bracket in response to an applied force, and at least one indicator which is visibly distortable in response to movement of the at least one and other portions of the bracket;
    an optical detector for optically detecting distortion of the indicator and issuing an output signal indicative of the relative resilient movement between the at least one and another portions of the bracket; and a processor which receives the output signal from the optical detector to provide an indication of magnitude and/or direction of the force applied to the orthodontic bracket, wherein the orthodontic bracket comprises a lower base member adapted to being affixed to a tooth, an upper bracket member, and an elastomeric layer interposed between the lower base and upper bracket members to allow for resilient movement of the upper bracket member relative to the lower base member in response to a force applied to the upper bracket member, and wherein the indicator comprises at least one fiducial mark for indicating relative movement between the lower base and upper bracket members, and wherein the at least one fiducial mark comprises registered lower and upper mark segments on the lower base and upper bracket members, respectively, wherein misregistry between the lower and upper mark segments is indicative of a force applied to the upper bracket member.

12. The system of claim 11, wherein the detector is a hand held optical detector.

13. The system of claim 12, wherein the hand held optical detector comprises a proximal handle and a distal wand having a wand tip adapted to be placed adjacent the at least one orthodontic bracket when affixed to a tooth.

14. The system of claim 13, wherein the hand held optical detector emits laser or ultraviolet radiation for to optically detect the indicator on the orthodontic bracket.

15. The system as in claim 11, wherein the at least one fiducial mark is formed of a phosphorescent or fluorescent material.

16. The system as in claim 11, wherein the at least one fiducial mark comprises registered grooves formed on opposing surfaces of the lower base and upper bracket members.

17. The system as in claim 16, wherein the registered grooves are V-shaped, rectangularly shaped or hem spherically shaped.

18. The system as in claim 16, wherein the processor provides an indication of the applied force relative to three mutually orthogonal axes and torque about such axes.

19. A method of determining magnitude and/or direction of a force applied to an orthodontic bracket comprising:

affixing an orthodontic bracket which is comprised of an elastomeric member which allows at least one portion of the bracket to be resiliently movable relative to at least one other portion of the bracket in response to an applied force, and at least one indicator which is visibly distortable in response to movement of the at least one and other portions of the bracket;

optically detecting distortion of the indicator and issuing an output signal indicative of the relative resilient movement between the at least one and other portions of the bracket; and processing the output signal from the optical detector to provide an indication of magnitude and/or direction of the force applied to the orthodontic bracket.

20. The method of claim 19, comprising providing an orthodontic bracket which comprises a lower base member adapted to being affixed to a tooth, an upper bracket member, and an elastomeric layer interposed between the lower base and upper bracket members to allow for resilient movement of the upper bracket member relative to the lower base member in response to a force applied to the upper bracket member.

21. The method as in claim 20, comprising providing registered lower and upper mark segments on the lower base and upper bracket members, respectively, wherein misregistry between the lower and upper mark segments is indicative of a force applied to the upper bracket member.

22. The method as in claim 20, comprising providing registered grooves formed on opposing surfaces of the lower base and upper bracket members as the indicator.

23. The method as in claim 22, wherein the registered grooves formed on opposing surfaces of the lower base and upper bracket members are V-shaped, rectangularly shaped or hemispherically shaped.

24. The method of claim 19, comprising positioning a hand held optical detector adjacent to the orthodontic bracket.

25. The method of claim 19, comprising scanning the indicator with laser or ultraviolet radiation issuing from the optical detector.

26. The method of claim 19, comprising providing at least one fiducial mark as the indicator for indicating relative movement between the at least one and other portions of the bracket.

27. The method as in claim 26 or 21, comprising forming the at least one fiducial mark of a phosphorescent or fluorescent material.

28. The method of claim 19, wherein the output signal is processed to provide an indication of the applied force relative to three mutually orthogonal axes and torque about such axes.

\* \* \* \* \*